(12) United States Patent
Inoue et al.

(10) Patent No.: US 6,373,916 B1
(45) Date of Patent: Apr. 16, 2002

(54) X-RAY CT APPARATUS

(75) Inventors: Yoshihiro Inoue; Eiichi Morita, both of Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/568,216

(22) Filed: May 9, 2000

(30) Foreign Application Priority Data

| May 10, 1999 | (JP) | ............................................. | 11-128704 |
| May 18, 1999 | (JP) | ............................................. | 11-137143 |
| May 18, 1999 | (JP) | ............................................. | 11-137144 |

(51) Int. Cl.[7] .............................................. G01N 23/00

(52) U.S. Cl. ............................................. 378/4; 378/20

(58) Field of Search ........................ 378/4–20

(56) References Cited

U.S. PATENT DOCUMENTS 5,457,724 A * 10/1995 Toth ............................... 378/4
6,041,097 A * 3/2000 Roos et al. .................... 378/19

* cited by examiner

*Primary Examiner*—Craig E. Church
(74) *Attorney, Agent, or Firm*—Rader Fishman & Grauer

(57) ABSTRACT

An X-ray CT apparatus for reconstructing images based on transmitted X-ray detection data acquired by emitting a conical X-ray beam from around an object and outputted from a flat panel X-ray sensor. In advance of CT imaging, a reconstruct area for CT imaging is displayed on a display monitor as superimposed on a fluoroscopic image acquired by irradiating the object with X rays emitted from a selected direction around the object. The operator can determine, before executing the CT imaging, whether a site of interest to be imaged is within the reconstruct area, thereby reliably acquiring CT images of desired sections.

9 Claims, 17 Drawing Sheets

X-RAY CT APPARATUS

BACKGROUND OF THE INVENTION (1) Field of the Invention

This invention relates to cone beam type X-ray CT apparatus for performing CT (computerized tomography of selected sections) by irradiating an object under examination such as a patient or an article with X rays emitted in a diverging cone form. More particularly, the invention relates to a technique for accurately determining a reconstruct area in advance of CT imaging.

(2) Description of the Related Art

X-ray CT apparatus widely used in hospitals and the like include, as shown in FIG. 1, an X-ray tube 71 for emitting a fan-shaped X-ray beam FB, and an X-ray line detector 73 with X-ray detecting elements 72 arranged in a row or a plurality of rows along a spreading direction of the X-ray beam. The X-ray tube 71 and X-ray line detector 73 are constantly opposed to each other across a patient M, and constitute an X-ray image pickup unit 74. In time of CT imaging, the X-ray tube 71 and X-ray line detector 73 revolve around the patient M, with the X-ray tube 71 emitting the fan-shaped X-ray beam FB, and the X-ray line detector 73 outputting transmitted X-ray detection data. A reconstruction process is performed to produce CT images based on the detection data. However, with X-ray CT apparatus shown in FIG. 1, since the fan-shaped X-ray beam FB has only a very small width, the X-ray image pickup unit 74 must be shifted along the body axis of patient M and revolved many times around the patient M in order to collect transmitted X-ray detection data necessary for a CT imaging covering a wide range. This inevitably consumes a long time in image pickup.

With this in view, an X-ray CT apparatus is being considered, which employs a wide conical X-ray beam instead of the fan-shaped X-ray beam FB, and a flat panel X-ray sensor (X-ray area sensor) instead of the X-ray line detector 73, the flat panel X-ray sensor having a large detection surface with X-ray detecting elements arranged in a matrix form. While the conical X-ray beam irradiates a site of interest of an object under examination all at once, the flat panel X-ray sensor having the large detection surface detects X rays transmitted through the site of interest all at once. This cone beam type X-ray CT apparatus can acquire transmitted X-ray detection data covering a wide range, with one rotation about the patient M of the X-ray image pickup unit. This results in a substantial reduction in image pickup time.

However, compared with the fan beam type X-ray CT apparatus, the conical beam type X-ray CT apparatus has a disadvantage that it is difficult to determine a reconstruct area in advance of CT imaging.

With CT imaging, overlapping portions of all X-ray beams emitted from around the body axis of patient M provide a reconstruct area, i.e. an imaging range, for making CT images of selected sections. It is therefore necessary, before starting an image pickup operation, to determine a reconstruct area carefully and confirm that a site of interest to be imaged is included in the reconstruct area. With the conical beam type X-ray CT apparatus, however, since it is difficult to determine a reconstruct area beforehand, an inconvenience could occur after an image pickup operation that CT images acquired fail to show desired sections, with the site of interest excluded from the reconstruct area.

Further, in a conventional practice of acquiring sectional images of patient M, a so-called scanning plan is made for a particular site of interest by setting an imaging range, positions from which sectional images are to be picked up, and sectional image pickup intervals of 10 mm, for example, based on a fluoroscopic image of patient M acquired beforehand. Based on the scanning plan, a relative position between the patient M and the apparatus is determined to be suitable for an image pickup starting position, and then the apparatus is operated.

In the conventional practice, however, while the scanning plan is based on a fluoroscopic image of patient M, an actual image pickup starting position is determined with reference to the position of patient M at that time rather than the fluoroscopic image. Consequently, an error in the position of patient M relative to the apparatus would result in a deviation of the imaging range, making desired sectional images impossible.

Furthermore, depending on patients M, diverse sites of interest may have to be imaged. These sites include, for example, one having a large imaging range transversely of the body, such as the whole stomach or the whole abdomen, one having a small imaging range transversely of the body but a large imaging range along the body axis, such as the gullet or the vertebra, and one having small imaging ranges both transversely of the body and along the body axis, such as the liver.

To cope with the varied situations, the X-ray CT apparatus includes an aperture or the like for the X-ray source to vary the size of a reconstruct area of X rays irradiating the patient M.

Conventionally, however, a reconstruct area of X rays is determined unequivocally according to an image pickup site when making a scanning plan. Particularly where the reconstruct area is small, an error tends to occur in the relative position between the reconstruct area of X rays and the patient M in time of actual image pickup, making desired sectional images impossible to acquire.

SUMMARY OF THE INVENTION

This invention has been made having regard to the state of the art noted above, and its primary object is to provide a conical beam type X-ray CT apparatus for accurately determining a reconstruct area in advance of CT imaging.

Another object of this invention is to allow desired sectional images to be acquired properly by correctly setting, to an object under examination, an imaging range and positions of sectional images to be reconstructed, based on a fluoroscopic image picked up of the object in time of actual imaging.

To fulfill the above objects, this invention provides the following constructions:

(1) An X-ray CT apparatus for picking up sectional images of an object by irradiating the object with a conical X-ray beam from around a body axis of the object and detecting X rays transmitted through the object, the apparatus comprising:

an X-ray image pickup device including an X-ray tube for emitting the conical X-ray beam to the object placed on a top board, and a flat panel X-ray sensor with X-ray detecting elements arranged in a matrix form for detecting transmitted X rays;

a drive device for driving the X-ray image pickup device about the body axis of the object;

an image reconstruct device for reconstructing a sectional image of a designated section based on transmitted X-ray detection data outputted from the flat panel X-ray sensor of the X-ray image pickup device driven in a fluoroscopic imaging mode;

an image display device for displaying X-ray images;

a fluoroscopic imaging device for acquiring a fluoroscopic image based on the transmitted X-ray detection data outputted from the flat panel X-ray sensor of the X-ray image pickup device driven in the fluoroscopic imaging mode, and displaying the fluoroscopic image on the image display device; and a reconstruct area superimposing device for displaying a reconstruct area for CT imaging as superimposed on the fluoroscopic image acquired by the fluoroscopic imaging device.

With the above apparatus according to the invention, a fluoroscopic imaging (simple X-ray imaging) operation is carried out first to acquire a fluoroscopic image for confirming a reconstruct area. That is, the X-ray image pickup device is set to an appropriate position for the fluoroscopic imaging mode, and the object is irradiated with a conical X-ray beam from the X-ray tube. The flat panel X-ray sensor detects a transmitted X-ray image. Based on the transmitted X-ray detection data outputted from the X-ray sensor, the fluoroscopic imaging device acquires a fluoroscopic image and displays it on the image display device. At this time, with the X-ray CT apparatus according to this invention, the reconstruct area superimposing device simultaneously displays a reconstruct area for CT imaging on the fluoroscopic image (i.e. superimposed display). Only an area where all conical X-ray beams emitted from around the body axis of the object overlap one another provides the reconstruct area (i.e. an imaging range). The reconstruct area corresponds to an entire inner area of a circle around the center (imaging center) of a gantry and inscribed in the conical X-ray beam. The reconstruct area, when superimposed on the fluoroscopic image, appears in a circular shape. That is, before starting the CT imaging, the operator may check whether or not a site of interest to be imaged is within the reconstruct area superimposed on the fluoroscopic image. The operator starts the CT imaging after confirming that the site of interest is within the reconstruct area. As a result, CT images of desired sections may be obtained reliably. In the CT imaging by the apparatus according to this invention, the site of interest to be imaged is irradiated with wide conical X-ray beams all at once, and X rays transmitted through the site of interest are detected all at once by a large detection surface of the flat panel X-ray sensor. Only a short imaging time is required since transmitted mitted X-ray detection data covering a wide range is collected quickly.

(2) Preferably, the apparatus (1) above further comprises a slice designating device for designating positions of sections for CT imaging on the fluoroscopic image with the reconstruct area superimposed thereon. With this construction, positions of sections of which CT images are to be made may be designated on the fluoroscopic image with the reconstruct area superimposed thereon to indicate a range for designating positions of sections. The operator can properly and simply designate positions of sections of which CT images are to be made by using the reconstruct area as a guide.

(3) Preferably, the apparatus (1) above further comprises prises an irradiating area superimposing device for displaying an area irradiated by the conical X-ray beam, as superimposed on the fluoroscopic image. With this construction, an area of the object irradiated by the conical X-ray beam from the X-ray tube may be displayed as superimposed on the fluoroscopic image. Thus, the operator may confirm an area of the object to be exposed to X rays.

(4) Preferably, the apparatus (1) above further comprises prises a moving device for moving the object along the body axis of the object relative to the X-ray image pickup device. With this construction, a fluoroscopic image may be acquired from a selected position along the body axis of the object.

(5) Preferably, the apparatus (4) above further comprises prises a fluoroscopic image composing device for composing and outputting one fluoroscopic image based on transmitted X-ray data corresponding to a plurality of images of the object acquired by driving the moving device to move the object. With this construction, where the site of interest of the object cannot fit into the irradiating area of the conical X-ray beam, a fluoroscopic image may be obtained in the fluoroscopic imaging mode from each of several overlapping or adjacent positions covering the site of interest. Main portions of a plurality of fluoroscopic images obtained as above may be combined to form one fluoroscopic image for display on the image display device. That is, the operator may carry out an operation based on one fluoroscopic image, without having to switch the image display device and the like frequently, which realizes an increased efficiency of operation.

(6) Preferably, the apparatus (4) above further comprises prises an imaging range setting device for setting an imaging range on the fluoroscopic image displayed on the display device, wherein the moving device is operable to move the object over the imaging range set by the imaging range setting device, and the slice designating device is operable to designate positions of sections within the imaging range.

With this construction, while confirming the reconstruct area displayed on the display device, the operator may designate positions of sections to be imaged, to acquire CT images in a desired range reliably.

(7) Preferably, the apparatus (6) above further comprises prises an irradiating field setting device for setting a field size of X rays to irradiate the object according to the reconstruct area. With this construction, the site of interest of the object to be imaged may be irradiated with a conical X-ray beam of a size suited to the size of the site of interest.

(8) Preferably, in the apparatus (7) above, the irradiating ating field setting device includes a collimator and an aperture drive device for setting a field size of the conical X-ray beam emitted from the X-ray tube. With this construction, the irradiating area of the X-ray beam for irradiating the object and the reconstruct area may be controlled easily by the operator.

(9) Preferably, the apparatus (8) above further comprises prises a scan mode selecting device, operable based on the field size of X rays set by the irradiating field setting device and the imaging range set by the imaging range setting device, to select a driving mode such that a single scan is carried out by driving the drive device with the moving device stopped when the field size along an axis of revolution of the X-ray image pickup device is larger than the imaging range, and a spiral scan is carried out by simultaneously driving the drive device and the moving device when the field size along the axis of revolution of the X-ray image pickup device is smaller than the imaging range.

With this apparatus, after setting a size of the reconstruct area of X rays emitted in a diverging conical form to the object and an imaging range of the object, the single scan or spiral scan is automatically selected based on a relationship between the size of the reconstruct area along the axis of revolution of the X-ray source and the imaging range, so as to cover the entire imaging range. Thus, sectional images may be picked up easily and effectively with minimal exposure to X rays regardless of the patient's physique, the size of the article and the size of the site of interest to be imaged. Particularly where the object is a patient, X-ray irradiation over a larger area than necessary may be avoided to provide an advantage of reducing the burden imposed on the patient.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

First Embodiment

A first embodiment of this invention will be described with reference to FIGS. 2 through 15.

Figure 2:
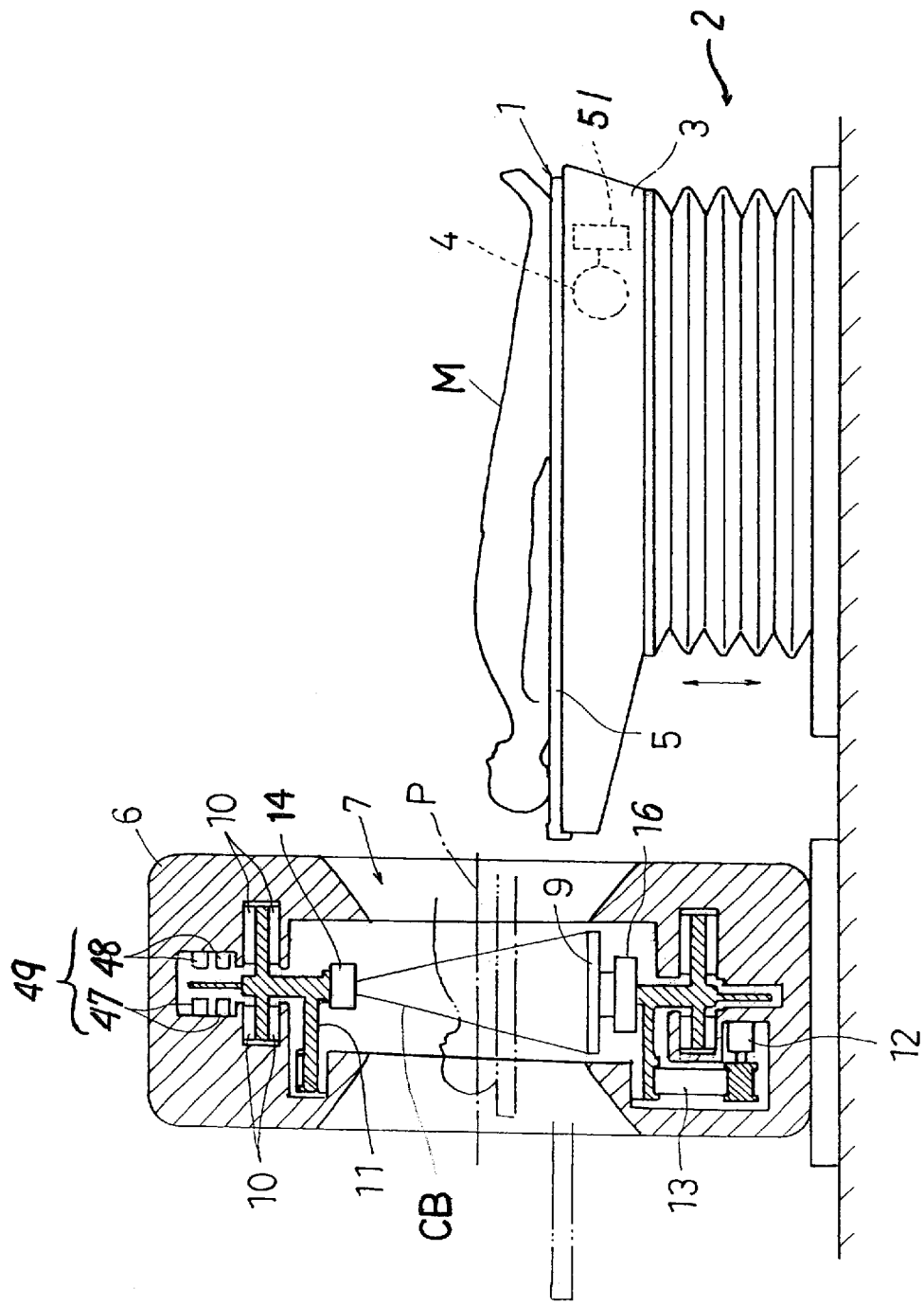
FIG. 2 is a schematic sectional view of an entire X-ray CT apparatus according to this invention.
Figure 3:
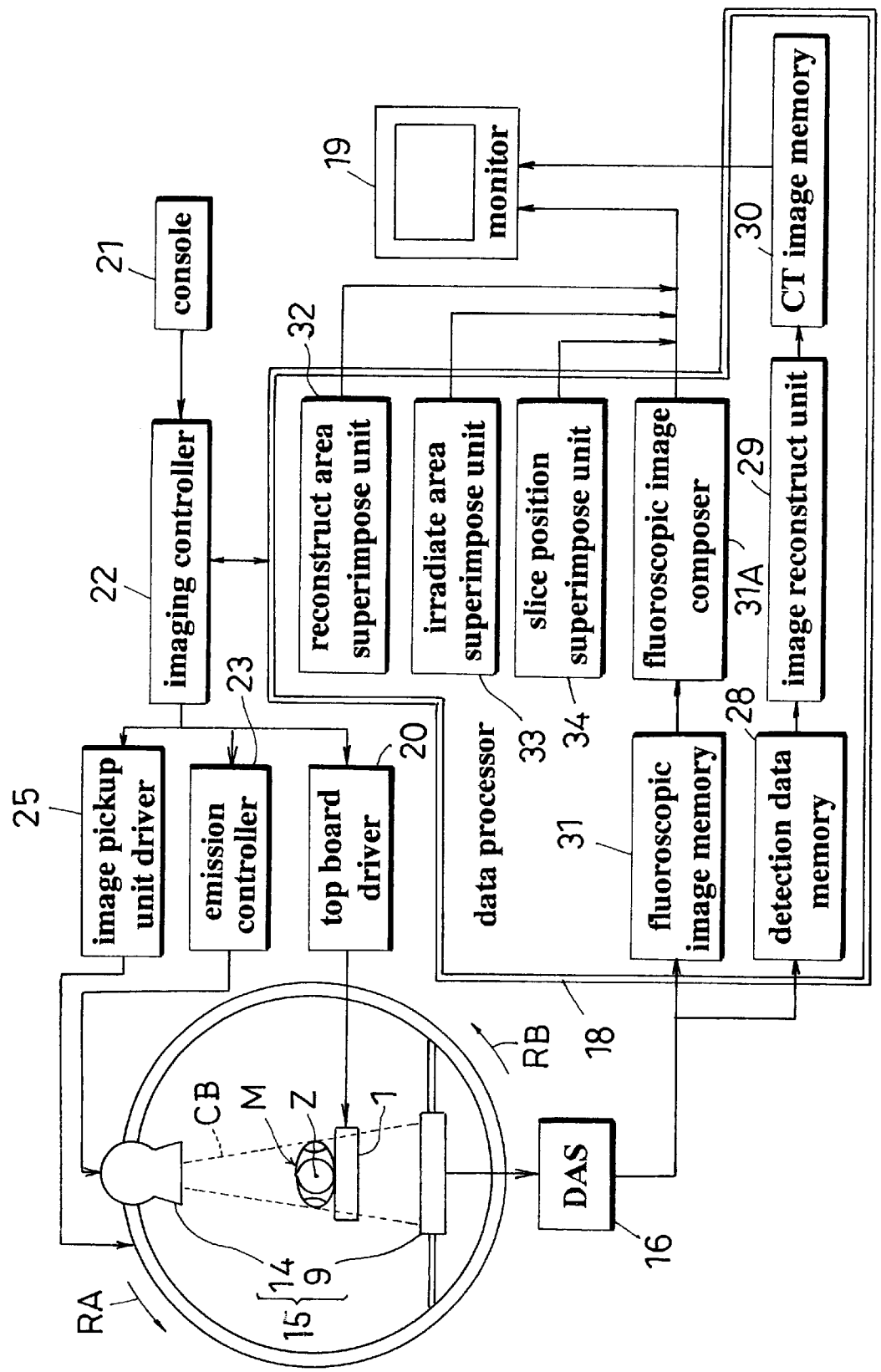
FIG. 3 is a block diagram of an entire X-ray CT apparatus in a first embodiment.
Figure 4A:
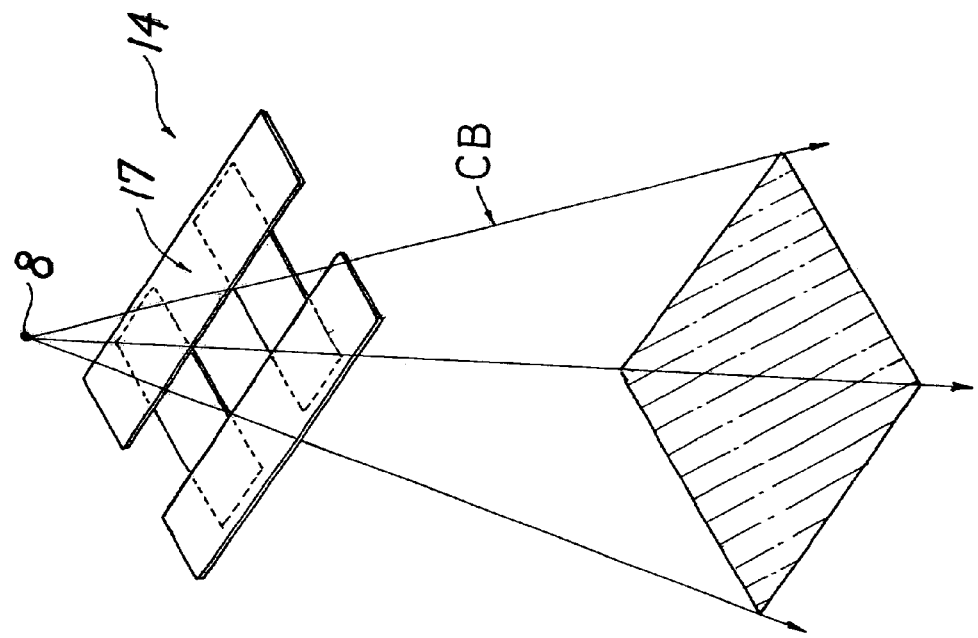
FIG. 4A is a schematic explanatory view showing a way of adjusting the shape of a conical X-ray beam used in the embodiment.
Figure 4B:
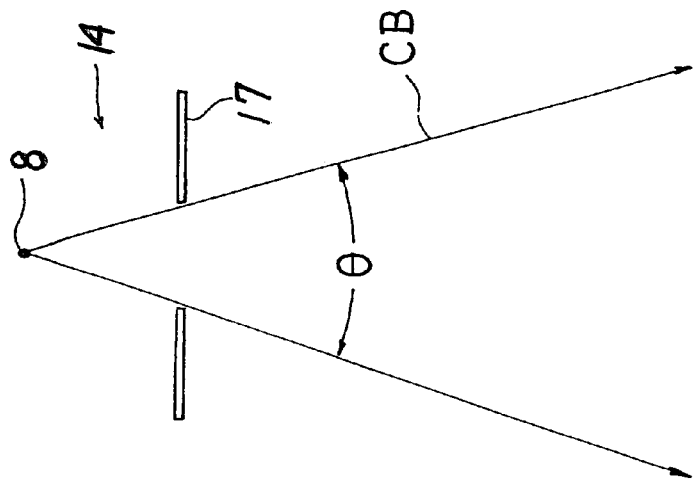
FIG. 4B is a schematic explanatory view showing an X-ray irradiating angle for adjusting an irradiating area of the conical X-ray beam used in the embodiment.
Figure 5:
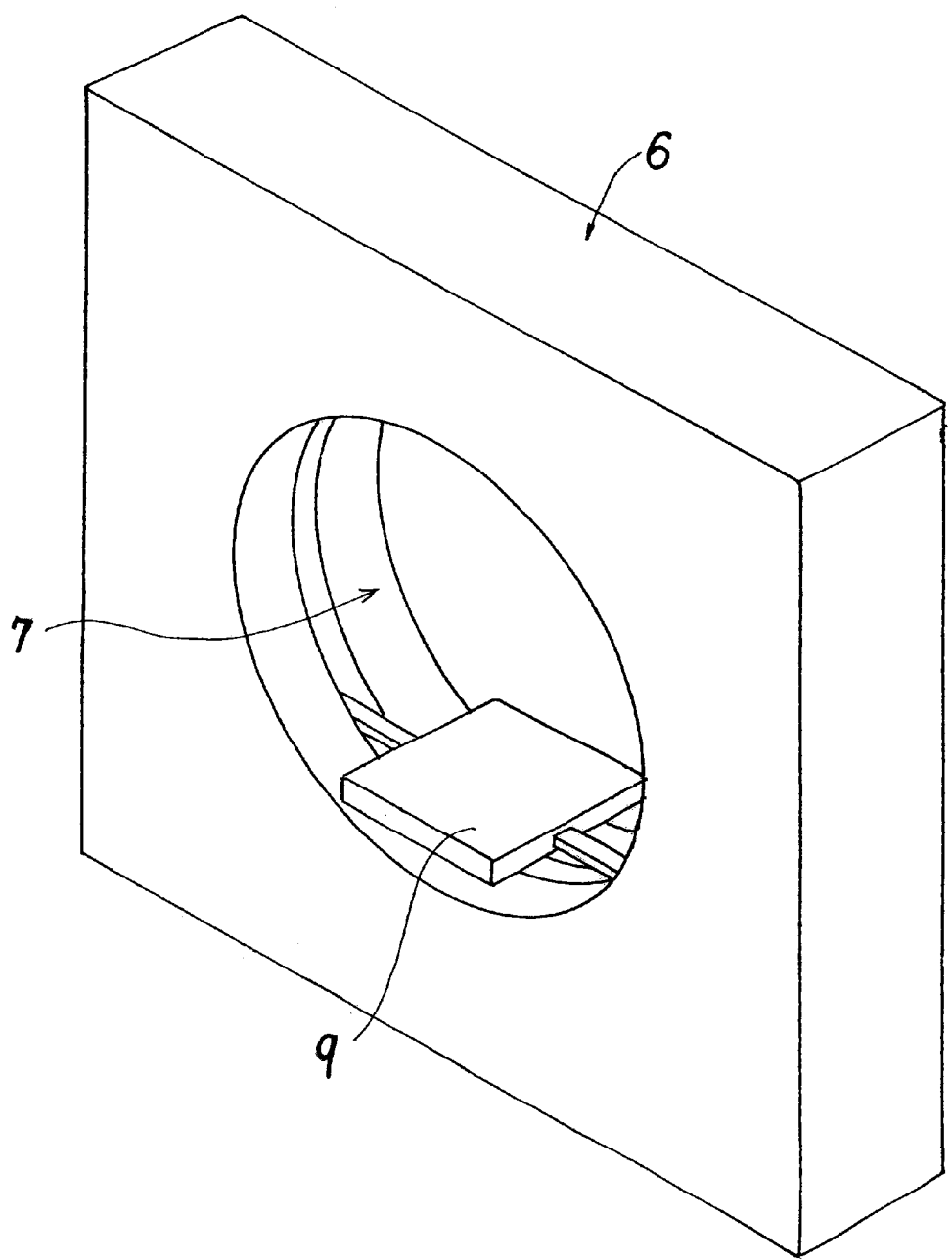
FIG. 5 is a perspective view of a gantry of the X-ray CT apparatus.
Figure 6:
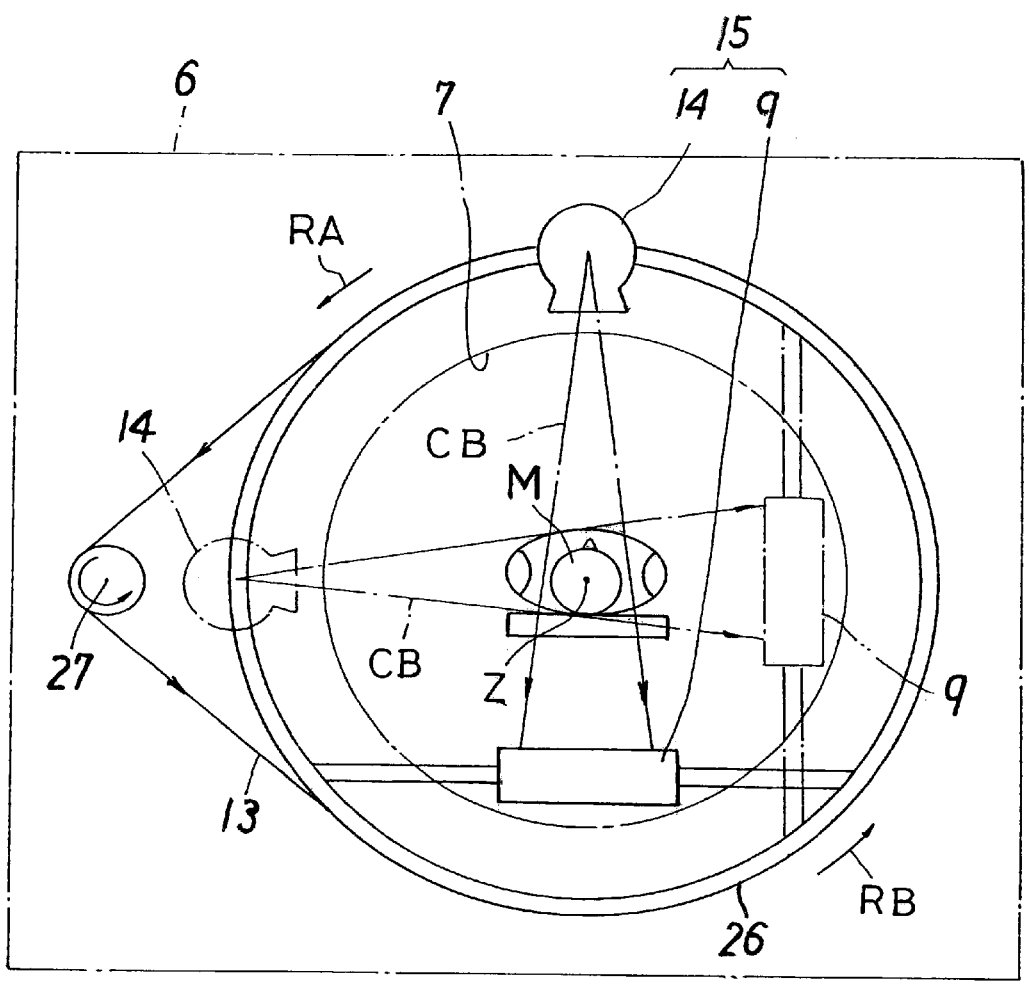
FIG. 6 is a schematic view showing movement of an X-ray image pickup unit of the X-ray CT apparatus.

FIG. 2 is a schematic sectional view of an entire X-ray CT apparatus according to this invention. FIG. 3 is a block diagram of the entire X-ray CT apparatus. FIGS. 4A and 4B are schematic explanatory views of a conical X-ray beam used in this embodiment. FIG. 5 is a perspective view of a gantry of the X-ray CT apparatus. FIG. 6 is a schematic view showing movement of an X-ray image pickup unit of the X-ray CT apparatus in this embodiment.

In the X-ray CT apparatus shown in FIG. 2, numeral 1 denotes a vertically movable bed for supporting a patent acting as an object M under examination. The bed 1 includes a base block 3 vertically movable by a lifting device 2 such as a motor, and a top board 5 mounted on the base block 3 to be horizontally movable, with the patient M placed thereon, by a reversible motor 4 acting as a moving device. The moving device may be in the form of an air cylinder or the like.

Figure 1:
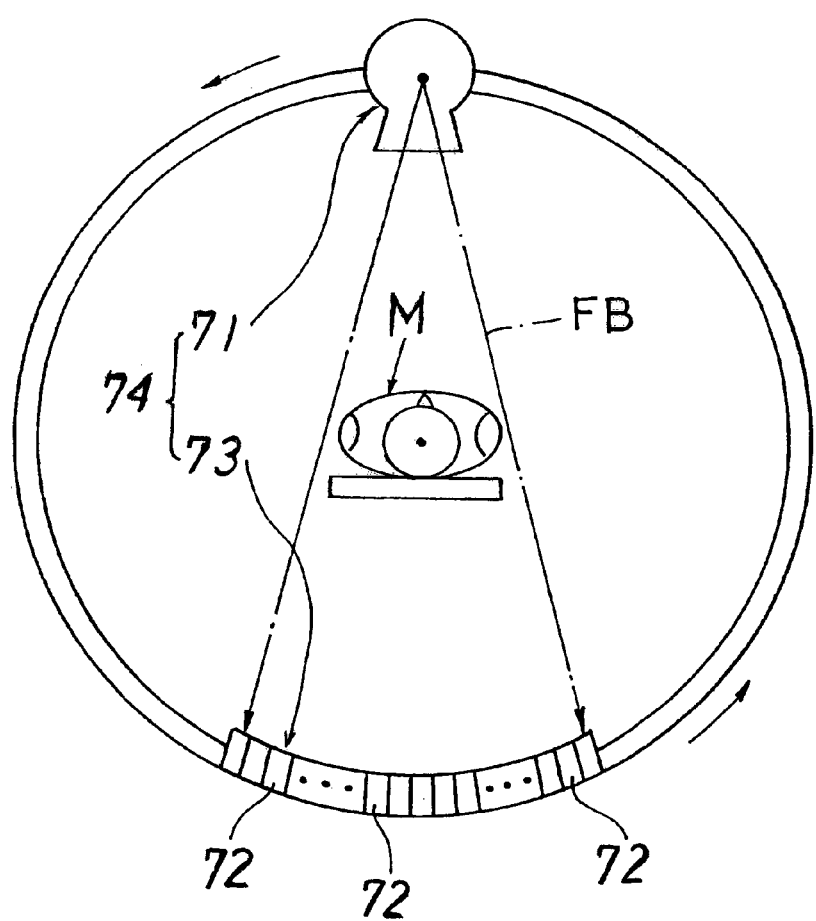
FIG. 1 is a schematic view showing an outline of an image pickup system in a conventional apparatus.

Numeral 6 in FIG. 1 denotes a gantry. The gantry 6 defines an opening 7 formed therethrough for receiving the top board 5 carrying the patient M. The gantry 6 supports an X-ray tube 14 and a flat panel X-ray sensor 9 arranged across the opening 7.

The gantry 6 includes an annular frame 11 mounted therein to be rotatable through ball bearings 10. The frame 11 is operatively connected to a rotating motor 12 acting as a driving device, through a belt 13. The frame 11 supports the X-ray tube 14 for irradiating the patient M with a conical X-ray beam CB, and the flat panel X-ray sensor 9 opposed to the X-ray tube 14 across the patient M for detecting transmitted X rays. The X-ray tube 14 and X-ray sensor 9 are revolvable together about a horizontal axis P, and constitute an X-ray image pickup unit 15. The flat panel X-ray sensor 9 has a data acquisition system (DAS) 16 connected thereto for collecting X-ray projection data detected by the flat panel X-ray sensor 9.

As shown in FIG. 4A, the X-ray tube 14 includes a collimator 17 formed of an X-ray shielding material and disposed forwardly of an X-ray source (X-ray focus) 8 for determining a horizontal sectional shape of the conical X-ray beam CB. In this embodiment, the conical X-ray beam CB is emitted in a quadrangular pyramid having a square horizontal section. As shown in FIG. 4B, the conical X-ray beam CB has a spreading angle θ which represents a width thereof and which is unequivocally determined by geometry (i.e. a geometric positional relationship) of the X-ray source 8 and collimator 17. The flat panel X-ray sensor (which will be referred to hereinafter also as "panel type X-ray sensor") 9, as described in detail hereinafter, is an X-ray area sensor having a large two-dimensional detection surface with numerous X-ray detecting elements arranged in a matrix form. Further, the X-ray CT apparatus in this embodiment includes, arranged downstream of the panel type X-ray sensor 9, the data acquisition system (DAS) 16 for collecting transmitted X-ray detection data, a data processor 18 for processing the transmitted X-ray detection data collected by the data acquisition system 16 to produce CT images or fluoroscopic images, and a display monitor (image display device) 19 for displaying the CT images, fluoroscopic images and so on. When the X-ray image pickup unit 15 is driven in a CT imaging mode, the display monitor 19 displays CT images on its screen. When the X-ray image pickup unit 15 is driven in a fluoroscopic mode, the display monitor 19 displays a fluoroscopic image on its screen.

The components of the X-ray CT apparatus in this embodiment will particularly be described hereinafter with reference to FIG. 3.

The top board 5, with the patient M placed thereon, is movable forward, backward, right, left, upward and downward under control of a top board driver 20. The top board driver 20 controls the movement of top board 5 based on a command signal outputted from an imaging controller 22 in response to an input made through a console 21. The X-ray tube 14 emits a conical X-ray beam CB to the patient M with set irradiating conditions under control of an emission controller 23 including a high voltage generator. The control operation of the emission controller 23 also is based on a command signal outputted from the imaging controller 22 in response to an input made through the console 21.

Referring to FIG. 5, the X-ray tube 14 of X-ray image pickup unit 15 is mounted inside a housing of gantry 6 and is invisible in the figure. The panel type X-ray sensor 9 is mounted in an exposed state in the space of the opening 7 of gantry 6. X rays from the X-ray tube 14 irradiate the patient M through a slit formed continuously along the circumferential direction in an inner surface of the housing. Under control of an image pickup unit driver 25, the X-ray tube 14 and panel type X-ray sensor 9, remaining opposed to each other, revolve together around the body axis Z of patient M in the direction indicated by arrows RA and RB. That is, as shown in FIG. 6, the X-ray tube 14 and panel type X-ray sensor 9 are rigidly attached to a rotary ring 26 mounted in the housing of gantry 6. The rotary ring 26 is rotated in the direction of arrows RA and RB by a pulley 27 and belt 13 with a torque received from a motor (not shown). The X-ray tube 14 and panel type X-ray sensor 9, remaining opposed to each other, are movable with the rotary ring 26. The control operation of the image pickup unit driver 25 also is based on a command signal outputted from the imaging controller 22 in response to an input made through the console 21. The emission controller 23 and image pickup unit driver 25 control the X-ray image pickup unit 15 in different manners for the CT imaging mode and fluoroscopic imaging mode.

In the control for the CT imaging mode, the X-ray tube 14 continuously irradiates the patient M with the conical X-ray beam CB while making one revolution around the body axis Z of patient M. The panel type X-ray sensor 9 revolving with the X-ray tube 14 continuously detects transmitted X rays. The X-ray irradiating angle to the patient M varies with the revolution of X-ray tube 14. As a result, the panel type X-ray sensor 9 detects transmitted X rays from the entire circumference of patient M which are necessary for making CT images.

Figure 9:
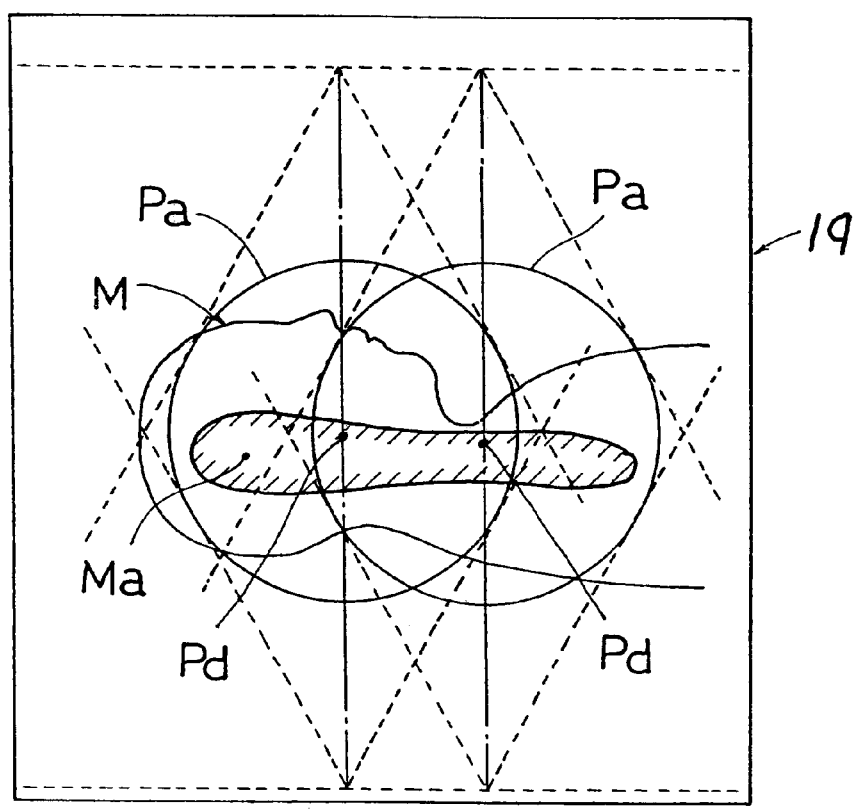
FIG. 9 is a view showing a composite image of fluoroscopic images picked up of two different parts.

In the control for the fluoroscopic imaging mode, as shown in dot and dash lines in FIG. 6, the X-ray tube 14 and panel type X-ray sensor 9 stand still as opposed to each other in an appropriate direction (a lateral direction in FIG. 9). In this state, the X-ray tube 14 irradiates the patient M with one conical X-ray beam CB at a time (or continuously as necessary). The panel type X-ray sensor 9 detects transmitted X rays for one screen. When a site of interest Ma does not fit into an irradiating area of the conical X-ray beam CB, the top board with the patient M lying thereon is moved under the X-ray image pickup unit 15 along the body axis of patient M. The above cycle of operations is repeated to acquire transmitted X-ray data for a plurality of images.

Next, the data processor 18 will particularly be described. The data processor 18 includes a detection data memory 28 for storing transmitted X-ray detection data outputted (in digital signals) from the data acquisition system 16 in time of the CT imaging mode, an image reconstruct unit 29 for performing a reconstruction process for making CT images based on the data stored in the detection data memory 28, a CT image memory 30 for storing the CT images of desired sections made by the image reconstruct unit 29, and a fluoroscopic image memory 31 for storing, as a fluoroscopic image, transmitted X-ray detection data outputted (in digital signals) from the data acquisition system 16 in time of the fluoroscopic imaging mode. The images stored in the CT image memory 30 and fluoroscopic image memory 31 are read therefrom and displayed on the screen of display monitor 19 at appropriate times. When the site of interest Ma has a size not fitting into one fluoroscopic image, as shown in FIG. 9, a fluoroscopic image is obtained from each of a plurality of overlapping or adjacent locations in the fluoroscopic imaging mode. Then, the main parts of two fluoroscopic images are combined by a fluoroscopic image composer 31A (i.e. a fluoroscopic image composing device) to displayed as one fluoroscopic image on the screen of display monitor 19.

Figure 7:
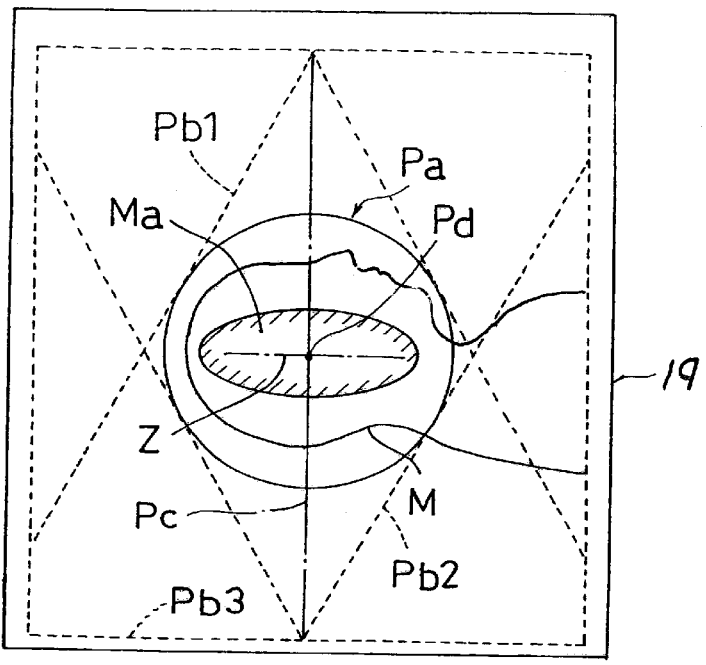
FIG. 7 is a view showing a fluoroscopic image with a reconstruct area superimposed thereon.

Further, in the X-ray CT apparatus of this embodiment, the data processor 18 includes, as characterizing features of this invention, a reconstruct area superimposing unit 32 for displaying a reconstruct area Pa for CT imaging as superimposed on the fluoroscopic image read from the fluoroscopic image memory 31, and an irradiate area superimposing unit 33 for displaying irradiate areas for CT imaging as superimposed on the fluoroscopic image. When the fluoroscopic image of patient M is displayed on the screen of display monitor 19, as shown in FIG. 7, the reconstruct area superimposing unit 32 and irradiate area superimposing unit 33 superimpose the reconstruct area Pa and irradiate areas Pb1–Pb3 on the fluoroscopic image.

The reconstruct area Pa is a region where X-ray beams irradiating the entire circumference of patient M all overlap one another. The reconstruct area Pa corresponds to the entire inner area of a circle around the center (imaging center) Pd of the gantry on an irradiation center line Pc and inscribed in the X-ray irradiate areas Pb1 and Pb2 The size of reconstruct area Pa may be derived in advance from the spreading angle θ of conical X-ray beam CB as shown in FIG. 4B, and a distance between the X-ray tube 14 and the center (imaging center) Pd of the gantry. Then, the reconstruct area Pa may be presented by describing, on the screen of display monitor 19, a circle having a size corresponding to the proportion of the fluoroscopic image to the screen. The operator may look at the screen shown in FIG. 7, and readily determine in advance whether the site of interest Ma fits in the reconstruct area Pa or not. This precludes the inconvenience that the site of interest Ma deviates from the imaging range. The X-ray irradiate areas Pb1–Pb3 are displayed as in the case of reconstruct area Pa. The X-ray irradiate area Pb1 represents an area exposed to X rays emitted from above. The X-ray irradiate area Pb2 represents an area exposed to X rays emitted from below. The X-ray irradiate area Pb3 represents an area exposed to X rays emitted from a side. Thus, the operator may look at the screen shown in FIG. 7, and readily check the exposed areas of patient M in advance.

Figure 8:
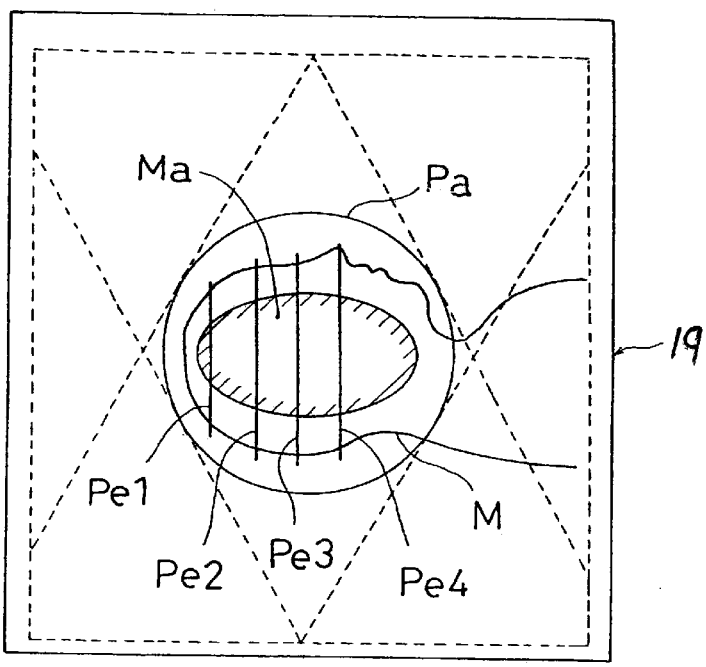
FIG. 8 is a view showing the fluoroscopic image with positions of sections designated for CT imaging and superimposed thereon.

Further, the X-ray CT apparatus in this embodiment includes a slice designating device for designating positions of sections for which CT images are to be made, on the fluoroscopic image with the reconstruct area Pa superimposed thereon. With the X-ray CT apparatus in this embodiment, when positions of sections for which CT images are to be made are designated on the fluoroscopic image with the reconstruct area Pa superimposed thereon, by cursor controls made through the console 21, as shown in FIG. 8, positions Pe1–Pe4 of sections designated through the console 21 for making CT images are displayed as lines superimposed on the fluoroscopic image. When CT imaging is executed, the image reconstruct unit 29 automatically makes CT images of the sections whose positions Pe1–Pe4 have been designated in advance. For this purpose, the data processor 18 includes a slice position superimposing unit 34 for displaying the positions Pe1–Pe4 of the sections designated through the console 21 for making CT images, as lines superimposed on the fluoroscopic image. Thus, the operator may properly and simply designate positions of the sections for making CT images, only by ensuring that such positions are included in an effective range indicated by the reconstruct area Pa displayed as superposed on the fluoroscopic image.

Figure 10:
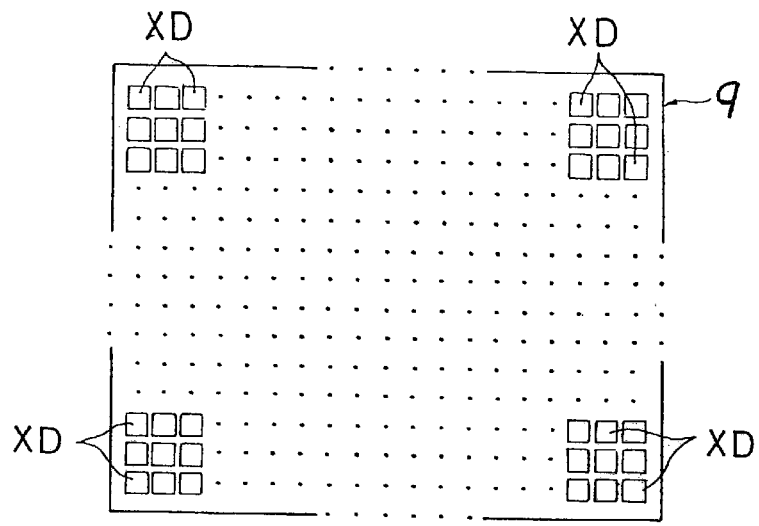
FIG. 10 is a plan view showing a basic construction of a panel type X-ray sensor used in the embodiment.

The panel type X-ray sensor 9 and adjacent components will be described next. As shown in FIG. 10, the panel type X-ray sensor 9 has X-ray detecting elements XD which may be arranged, for example, in a square matrix of 1024 in each row (x) and 1024 in each column (y). The size of X-ray sensor 9 may be in the order of 50 cm by 50 cm, for example.

Figure 11A:
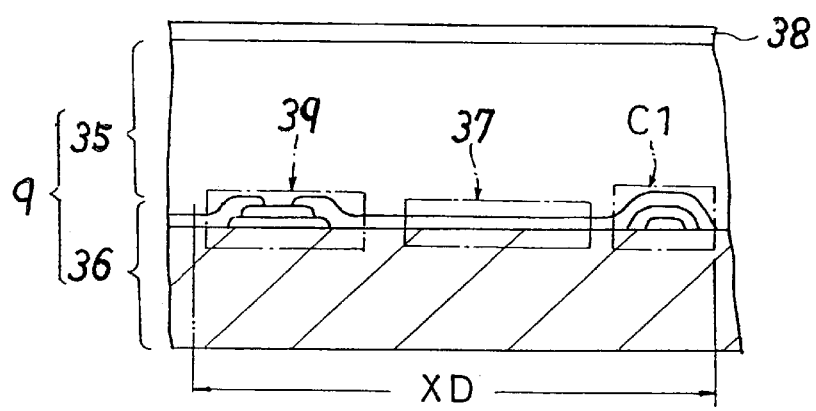
FIG. 11A is a sectional view showing a layer structure of a direct conversion type, panel type X-ray sensor.
Figure 11B:
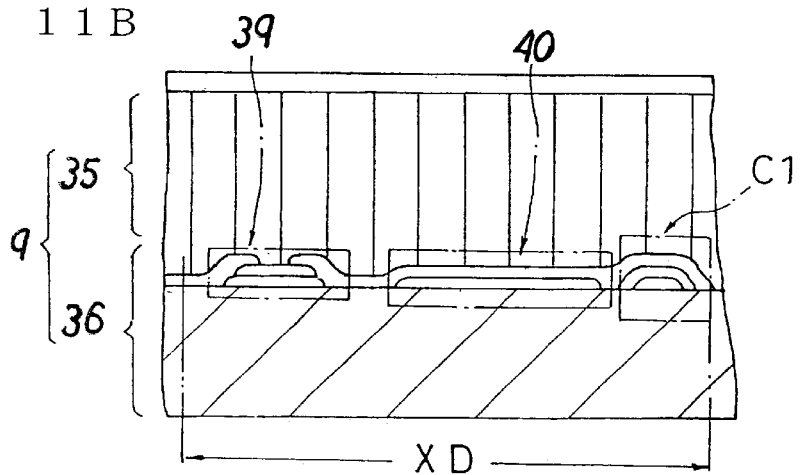
FIG. 11B is a sectional view showing a layer structure of an indirect conversion type, panel type X-ray sensor.

As shown in FIGS. 11A and 11B, the panel type X-ray sensor 3 has a laminated structure including an X-ray conversion layer 35 for converting incident X rays into electric charges or light, and a detection array layer 36 with elements arranged in a matrix form for detecting the charges or light generated by the X-ray conversion layer 35. The X-ray sensor 3 may be the direct conversion type shown in FIG. 11A or the indirect conversion type shown in FIG. 1B. In the former, direct conversion type, the X-ray conversion layer 35 comprises a selenium layer or CdZnTe layer for directly converting incident X rays into electric charges. The detection array layer 36 has charge collecting electrodes arranged on a surface thereof to act as charge detecting elements 37 opposed to a surface electrode 38. The charges detected are stored in capacitors Cl from which the charges may be fetched through TFTs (thin film transistors) 39. Each charge detecting element 37, part of the X-ray conversion layer 35 there above, capacitor Cl and TFT 39 constitute one X-ray detecting element XD.

In the latter, indirect conversion type, the X-ray conversion layer 35 comprises a scintillator layer for converting incident X rays into light. The detection array layer 36 has photodiodes formed on a surface thereof to act as photo detecting elements 40 for detecting the light, and storing charges in capacitors Cl. The charges stored are taken out through TFTs 39. Each photo detecting element 40, part of the X-ray conversion layer 35 there above, capacitor Cl and TFT 39 constitute one X-ray detecting element XD.

Figure 12:
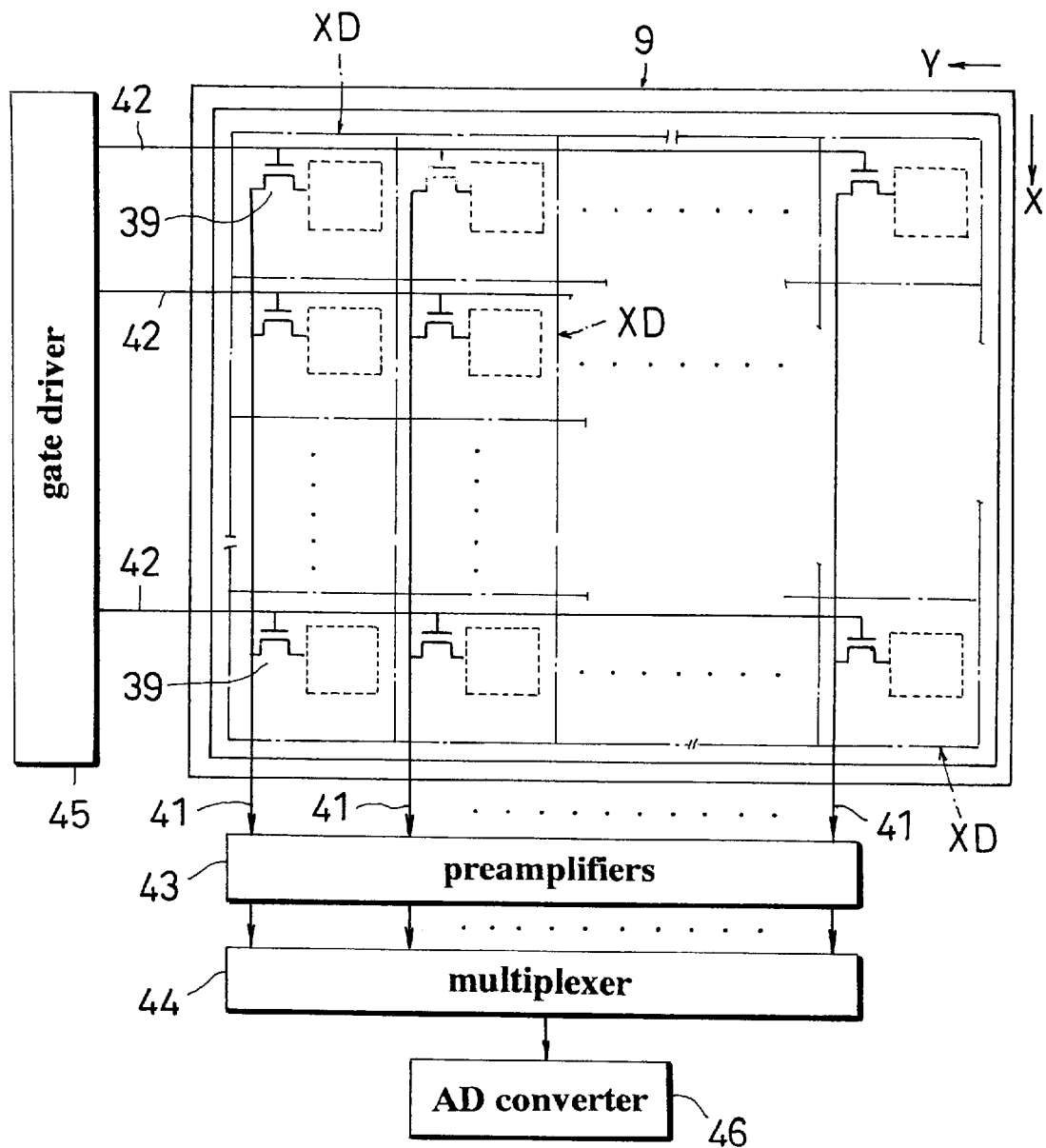
FIG. 12 is a block diagram showing a construction around the panel type X-ray sensor.

Further, as shown in FIG. 12, the source of thin film transistor 39 of each X-ray detecting element XD is connected to a read line 41 extending in X direction, with the gate connected to a read line 42 extending in Y direction. The read lines 41 are connected to a multiplexer 44 through preamplifiers 43. The read lines 42 are connected to a gate driver 45. The multiplexer 44 and gate driver 45 receive carrier-fetching scan signals. The X-ray detecting elements XD of panel type X-ray sensor 9 are identified by addresses (e.g. 0–1023) sequentially allocated to the X-ray detecting elements XD in the X and Y directions. Thus, each fetching scan signal designates an address in the X direction or Y direction.

In response to scan signals for Y direction, the gate driver 45 applies a fetching voltage to read lines 42 in the Y direction to select X-ray detecting elements XD column by column. The multiplexer 44 is switched in response to scan signals for the X direction. As a result, carriers (electrons or carriers) stored in the capacitors Cl of X-ray detecting elements XD in the selected columns are successively transmitted through the preamplifiers 43 and multiplexer 44, and are digitized by an analog-to-digital converter 46 to be outputted as transmitted X-ray detection signals.

It will be appreciated from the above description that the method of fetching carriers from the panel type X-ray sensor 9 is roughly analogous to that employed for ordinary imaging devices such as TV cameras. The preamplifiers 43, multiplexer 44, gate driver 45 and analog-to-digital converter 46 constitute the data acquisition system 16.

Figure 13:
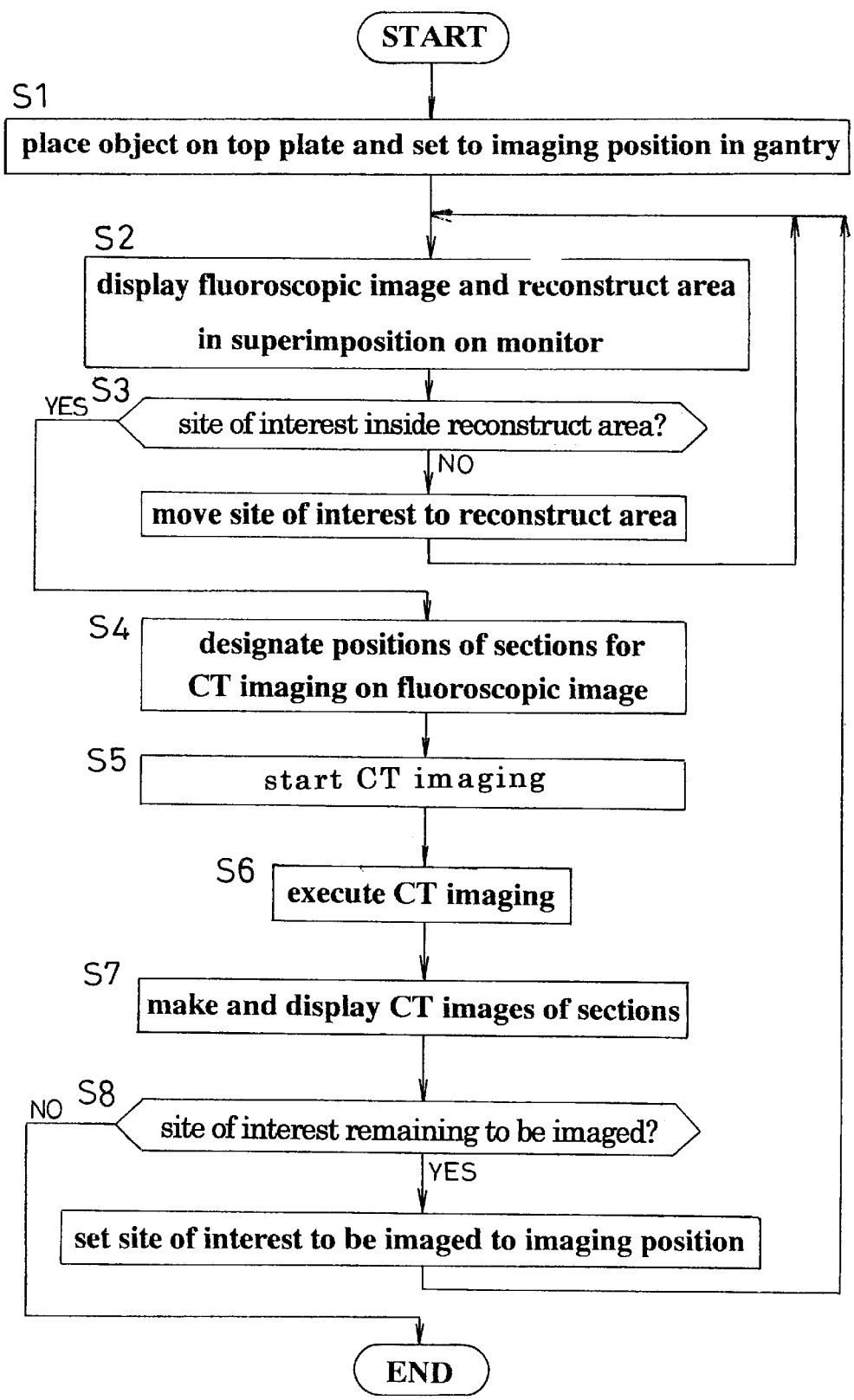
FIG. 13 is a flow chart showing a sequence of X-ray imaging in the embodiment.

The X-ray CT apparatus in this embodiment may further include, as necessary, a laser image printer (not shown) for printing CT images and/or fluoroscopic images on film and outputting such images as X-ray photographs, and an image storage memory (not shown) for storing CT images and/or fluoroscopic images in the form of image signals. Next, an X-ray imaging operation of the X-ray CT apparatus in this embodiment having the above construction will be described with reference to the drawings. FIG. 13 is a flow chart showing a sequence of X-ray imaging carried out by the apparatus in this embodiment.

[Step S1] After placing the patient M on the top board 5, the top board 5 is moved to set the patient M to an imaging position in the gantry 6.

Figure 14:
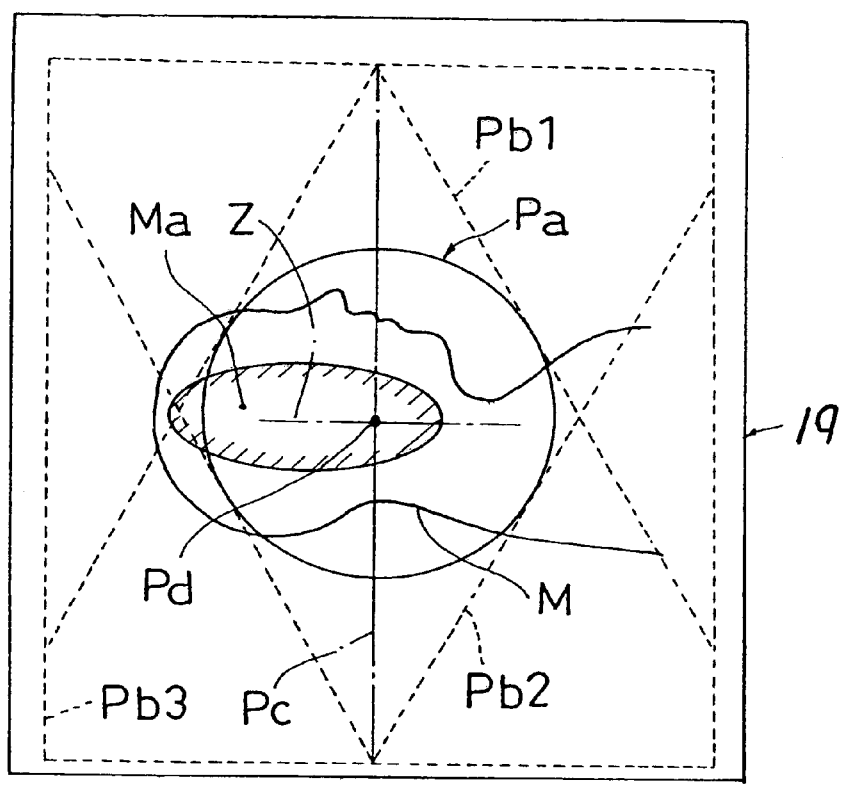
FIG. 14 is a view showing a situation where a site of interest fails to fit into a reconstruct area.

[Step S2] The X-ray image pickup unit 15 is driven in the fluoroscopic imaging mode to irradiate the patient M with a conical X-ray beam CB from a lateral direction and acquire a fluoroscopic image. As shown in FIG. 14, the fluoroscopic image is displayed on the screen of display monitor 19 with a reconstruct area Pa superimposed on the image.

[Step S3] The operator checks on the screen of display monitor 19 whether the site of interest Ma of patient M fits in the reconstruct area Pa. When the site of interest Ma deviates from the reconstruct area Pa as shown in FIG. 14, the patient M is moved slightly and the operation returns to step S2. When the site of interest Ma is inside the reconstruct area Pa as shown in FIG. 7, the operation proceeds to step S4.

[Step S4] The operator controls the cursor through the console 21 to designate the positions Pe1–Pe4 of sections for making CT images as shown in FIG. 8.

[Step S5] The operator operates the console 21 to start CT imaging.

[Step S6] The X-ray image pickup unit 15 is driven in the CT imaging mode to execute CT imaging.

[Step S7] The image reconstruct unit 29 performs data processing based on X-ray detection data outputted from the panel type X-ray sensor 9. CT images of the designated positions Pe1–Pe4 of the sections are made and displayed on the screen of display monitor 19.

[Step S8] If there is another site of interest to be imaged next, the top board 5 is moved to set the site of interest of patient M to the imaging position in the gantry 6, and the operation returns to step S2. If there is no more site of interest to be imaged, the X-ray imaging is terminated.

Figure 15:
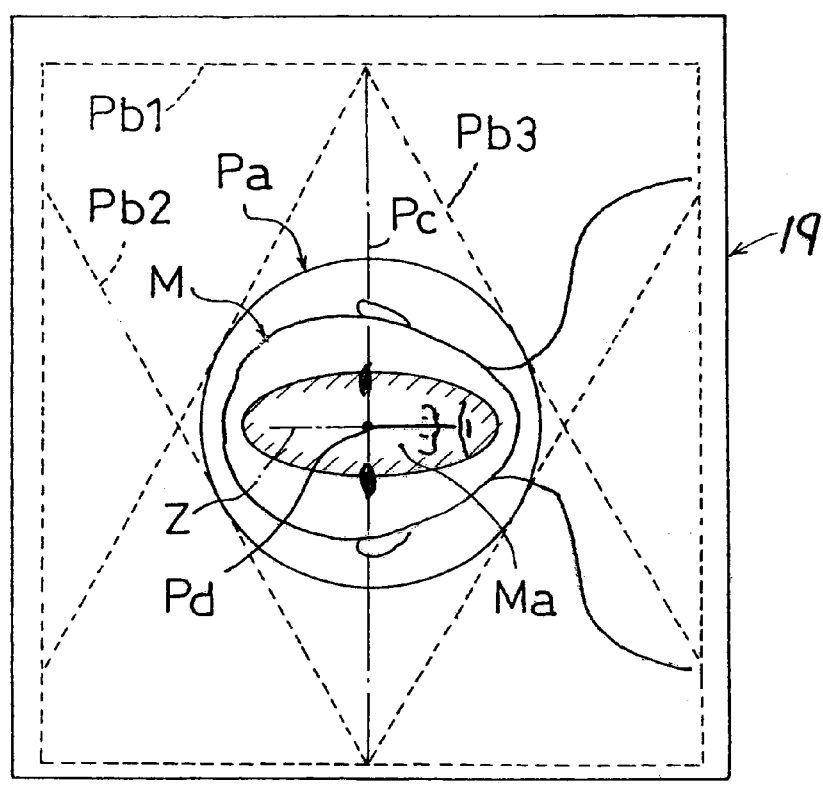
FIG. 15 is a view showing a fluoroscopic image produced by X rays emitted from above.

This invention is not limited to the above embodiment, but may be modified as follows:

(1) In the fluoroscopic imaging mode of the apparatus in the foregoing embodiment, the patient M is irradiated with a conical X-ray beam emitted from a side (i.e. from a lateral direction to acquire a fluoroscopic image for display with a reconstruct area Pa. The fluoroscopic image to be displayed with the reconstruct area Pa is not limited to the image acquired by irradiating the patient M with a conical X-ray beam from a side. The apparatus may be modified, for example, to irradiate the patient M with a conical X-ray beam emitted from above. Then, as shown in FIG. 15, a fluoroscopic image picked up from the front of patient M may be displayed on the screen of display monitor 19 with the reconstruct area Pa superimposed on the image.

(2) The flat panel type X-ray sensor 9 of the X-ray CT apparatus of this invention is not limitative.

(3) The X-ray CT apparatus in this invention is not limited to one used for picking up images from patients for medical purposes. The CT apparatus is applicable also to a non destructive inspection for picking up images from articles to detect flaws. The patients, articles and so on are herein collectively called objects under examination.

Second Embodiment

Aspects of this embodiment different from the first embodiment will be described in detail with reference to FIGS. 2 and 17 through 19.

As shown in FIG. 2, this embodiment further includes two optical sensors 49 mounted in an upper portion of gantry 6 and each having a light transmitter 47 and a light receiver 48 for detecting a position of X-ray tube 14. The moving motor 4 has a rotary encoder 51 attached thereto for detecting an amount of rotation thereof, and hence an amount of movement of top board 5.

The specific construction of this embodiment will be described next.

Figure 16:
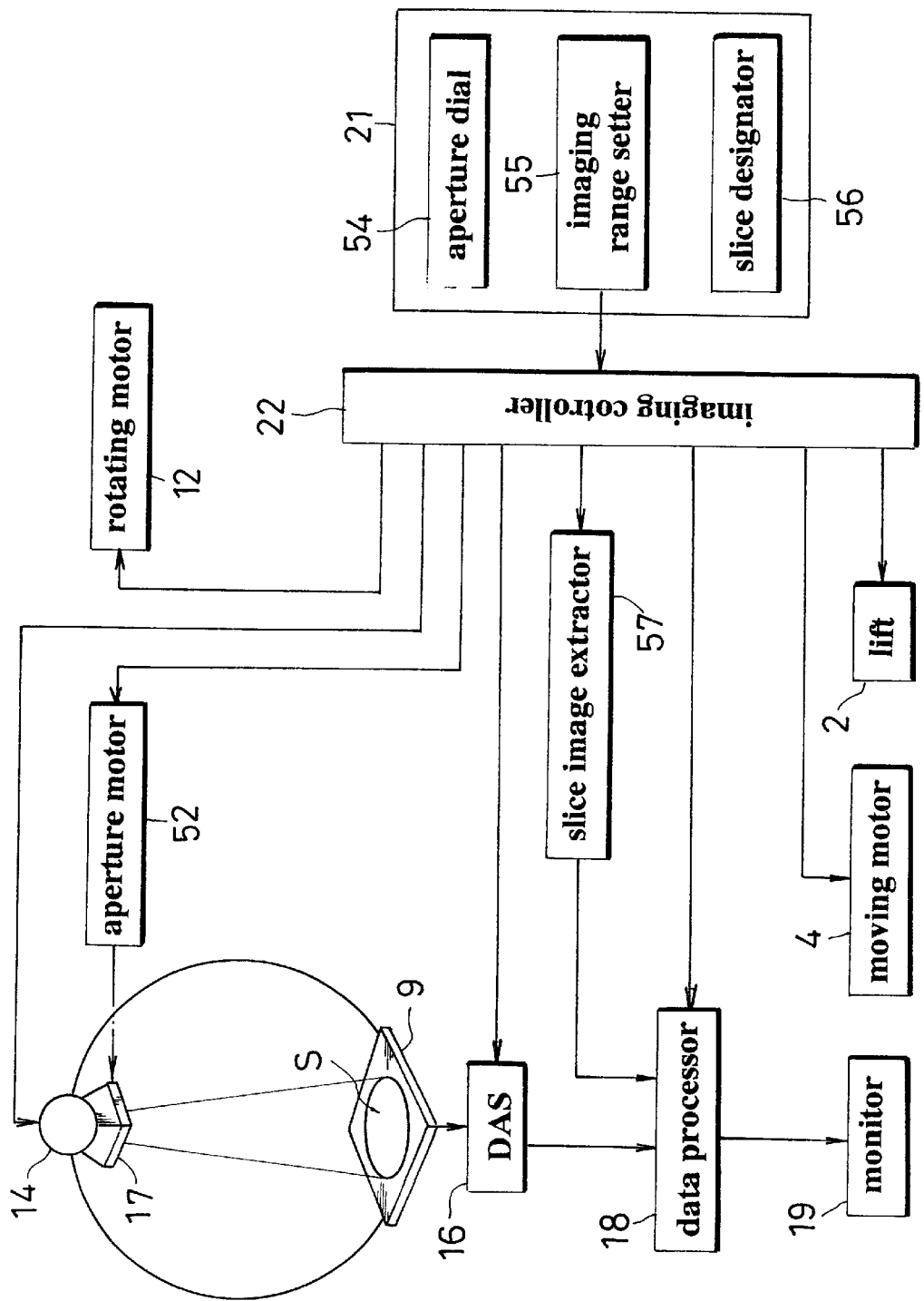
FIG. 16 is a block diagram showing an outline of an X-ray CT apparatus in a second embodiment.
Figure 17A:
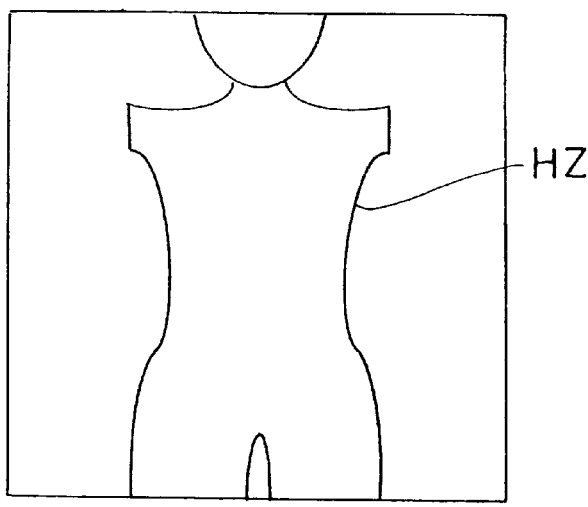
FIG. 17A is a front view of a fluoroscopic image.
Figure 17B:
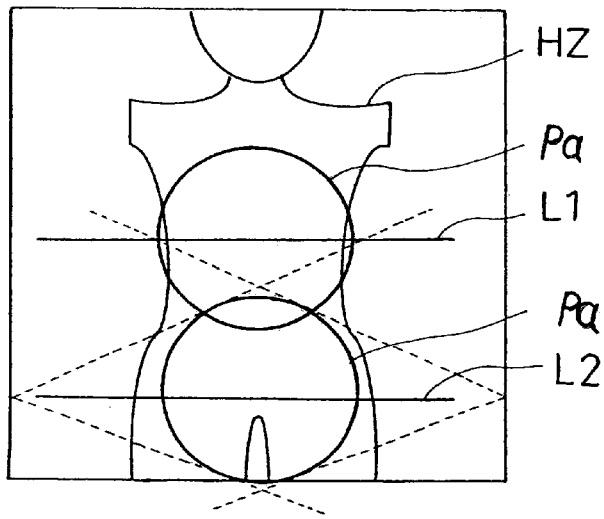
FIG. 17B is a view showing a way of designating an imaging range for sectional images from reconstruct areas on two fluoroscopic images.
Figure 17C:
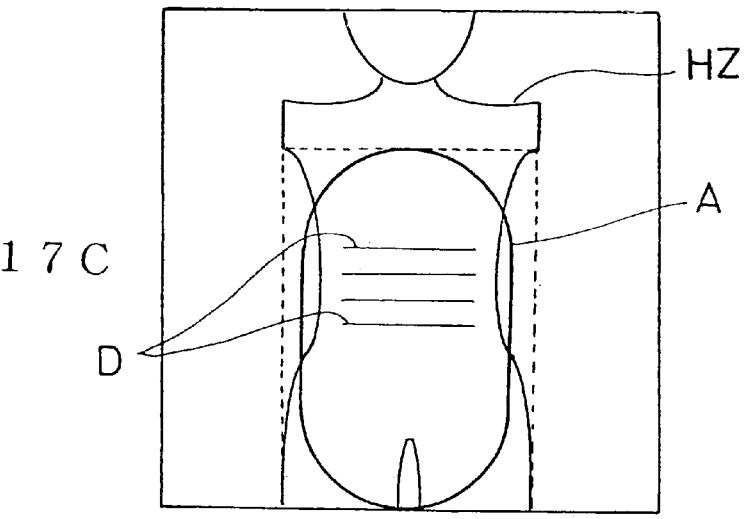
FIG. 17C is a view showing a way of picking up sectional images at intervals set within the imaging range displayed as superposed on a composite image of the two fluoroscopic images.

FIG. 16 is a block diagram showing an outline of the X-ray CT apparatus in the second embodiment. This apparatus includes the X-ray tube 14 for emitting X rays, and a collimator 17 for limiting a reconstruct area Pa for the X rays emitted from the X-ray tube 14. Thus, X rays are emitted in a diverging conical form (in a circular cone) to the square flat panel X-ray sensor 9.

As shown in FIG. 16, a data acquisition system 16 has a data processor 18 connected thereto for reconstructing fluoroscopic images and sectional images based on the projection data collected by the system 16. The data processor 18 has a display monitor 19 connected thereto for displaying the fluoroscopic images and sectional images reconstructed by the data processor 18, with a reconstruct area Pa superimposed on the fluoroscopic images. The reconstruct area Pa is movable relative to a fluoroscopic image displayed. while visually confirming the position of reconstruct area Pa based on the fluoroscopic image, the operator may operate an imaging range setter 55 to set an image pickup starting position and an image pickup finishing position. Similarly, while visually confirming the position of reconstruct area Pa based on the fluoroscopic image, the operator may operate a slice designator 56 to set positions of slice or sectional images to be reconstructed.

This apparatus includes a collimator 17 and an aperture motor 52 acting as an irradiating field setting device for setting a field size for X rays emitted from the X-ray tube 14 to the patient M. The field of X rays (and thus the size of a reconstruct area) may be changed according to the size of an article or the size of patient M to be imaged. The above irradiating field setting device may comprise a set of elements switchable by voltage application from a transmitting state to a non-transmitting state.

A lifting device 2, moving motor 4, rotating motor 12, data acquisition system 16, X-ray tube 14, data processor 18 and aperture motor 52 are connected to an imaging controller 22. A console 21 also is connected to the imaging controller 22. Though not shown in FIG. 16, the optical sensors 49 and rotary encoder 51 also are connected to a control unit 53.

The console 21 includes an aperture dial 54 for driving the aperture motor 52 to adjust an aperture, and the imaging range setter 55 and slice designator 56 each having a set key and a termination key. Further, a set slice image extractor 57 is connected to the control unit 53. The set slice image extractor 57 and data processor 18 are connected to each other. Based on the positions of sectional images set by the slice image designator 56, the data processor 18 reconstructs sectional images corresponding to these positions for display on the display monitor 19.

Next, a sequence of picking up sectional images by the above construction will be described.

The X-ray tube 14 is fixed to an uppermost position, and the aperture dial 54 is operated to maximize the field size of X rays by the collimator 17. In the case of a small patient M, for example, the aperture may be reduced as appropriate as long as a field is secured to cover the chest and abdomen. With the patient M placed in position, the lift device 2 is driven to raise the bed base block 3 to a position below the axis of revolution P. Subsequently, the moving motor 4 is driven to move the top board 5 toward the gantry 6. X rays are emitted from the X-ray tube 14 to irradiate a predetermined irradiation starting position for image pickup, such as the head or chest. The X rays are detected by the flat panel X-ray sensor 9. Projection data of the X rays detected are collected by the data acquisition system 16. Based on the projection data collected, the data processor 18 reconstructs a fluoroscopic image. The fluoroscopic image HZ is displayed on the display monitor 19 as shown FIG. 17A which is a front view showing an example of display. The bed base block 3 is raised only to a position below the axis of revolution P as noted above, in order to place the top board 5 as close to the flat panel X-ray sensor 9 as possible so that the X-ray tube 14 may irradiate the patient M over an extended range.

Next, the moving motor 4 is reversed to return the top board 5 to the irradiation starting position. The lift device 2 is driven to set the body axis Z of patient M to the axis of revolution P. That is, the top board 5 is raised to the same position as for picking up sectional images. In this state, a reconstruct area Pa is displayed on the fluoroscopic image HZ. While confirming the position of reconstruct area Pa relative to the fluoroscopic image HZ, the operator turns the aperture dial 54 to adjust the size of reconstruct area Pa to the site of interest to be imaged. [see FIG. 17B].

Subsequently, while confirming the position of reconstruct area Pa relative to the fluoroscopic image HZ, the reconstruct area Pa is moved to and stopped in a position for starting image pickup, and then the set key is operated. Further, the reconstruct area Pa is moved to and stopped in a position for finishing the image pickup, and the termination key is operated. The imaging range setter 55 is operated to set an image pickup starting position L1 and an image pickup finishing position L2. These positions L1 and L2 are displayed on the display monitor 19. [See FIG. 17B]. Next, the images are switched to display, on the display monitor 19, a reconstruct area A determined from the above image pickup starting position L1 and image pickup finishing position L2. While visually confirming the reconstruct area A, the operator presses the set key and termination key with the center of circular reconstruct area Pa set to the image pickup starting position of a region of which sectional images are to be picked up. Then, the operator sets through the slice designator 56 positions of sectional images to be reconstructed, and causes such positions D to be displayed on the display monitor 19. [see FIG. 17C]. Only the image pickup starting position of a region of which sectional images are to be picked up is set as described above, because a position for finishing the sectional image pickup for reconstruction is fixed as a matter of course since intervals between the sectional images to be picked up are determined beforehand in a scanning plan according to the site of interest. After the above setting operation, the top board 5 is moved horizontally by the moving motor 4 to adjust the positions of patient M and X-ray tube 14 to the image pickup starting position.

Subsequently, the X-ray tube 14 is driven to emit X rays, while driving the moving motor 4 and rotating motor 12, to execute a so-called spiral scan. Sectional images of the selected positions are automatically reconstructed and displayed on the display monitor 19. When the size of reconstruct area Pa is larger than the imaging range along the body axis Z of patient M and covers the entire imaging range, a so-called single scan may be carried out by driving the X-ray tube 14 to emit X rays with the moving motor 4 stopped and only the rotating motor 12 driven.

With the above construction, an imaging range and positions of sectional images to be reconstructed may be set while confirming a relative position between the fluoroscopic image HZ and reconstruct area Pa of patient M displayed in superimposition on the display monitor 19 in time of image pickup. Thus, the setting operation is carried out easily and properly.

This invention is not limited to the above embodiment, but may be modified as set out hereunder. In the above embodiment, the X-ray tube 14 emits X rays in a diverging circular cone. It is in accordance with this invention as long as X rays are emitted in a diverging conical form including, for example, a diverging quadrangular pyramid.

(1) The X-ray CT apparatus according to this invention is not limited to the above embodiment where the X-ray tube 14 and flat panel X-ray sensor 9 are mounted in the gantry 6 to be revolvable together. Various modifications are possible for this arrangement. For example, the X-ray tube 14 may be attached to one end and the flat panel X-ray sensor 9 attached to the other end of a C-shaped arm rotatable through an angle larger than 180 degrees. In another modified example, only the X-ray tube 14 is made revolvable, with the flat panel X-ray sensor 9 having a large width (e.g. 50 cm or more) along the axis of revolution P and formed annular and fixed to extend through the entire circumference.

(2) The X-ray CT apparatus according to this invention may be adapted to rotate an object under examination relative to the X-ray tube 14 and flat panel X-ray sensor 9. Further, the X-ray tube 14 and flat panel X-ray sensor 9 may be adapted movable along the axis of revolution P relative to the object under examination.

The axis of rotation P of the article or patient M rotatable relative to the X-ray tube 14 and flat panel X-ray sensor 9 also is called the axis of revolution P of X-ray tube 14.

Third Embodiment

Figure 18:
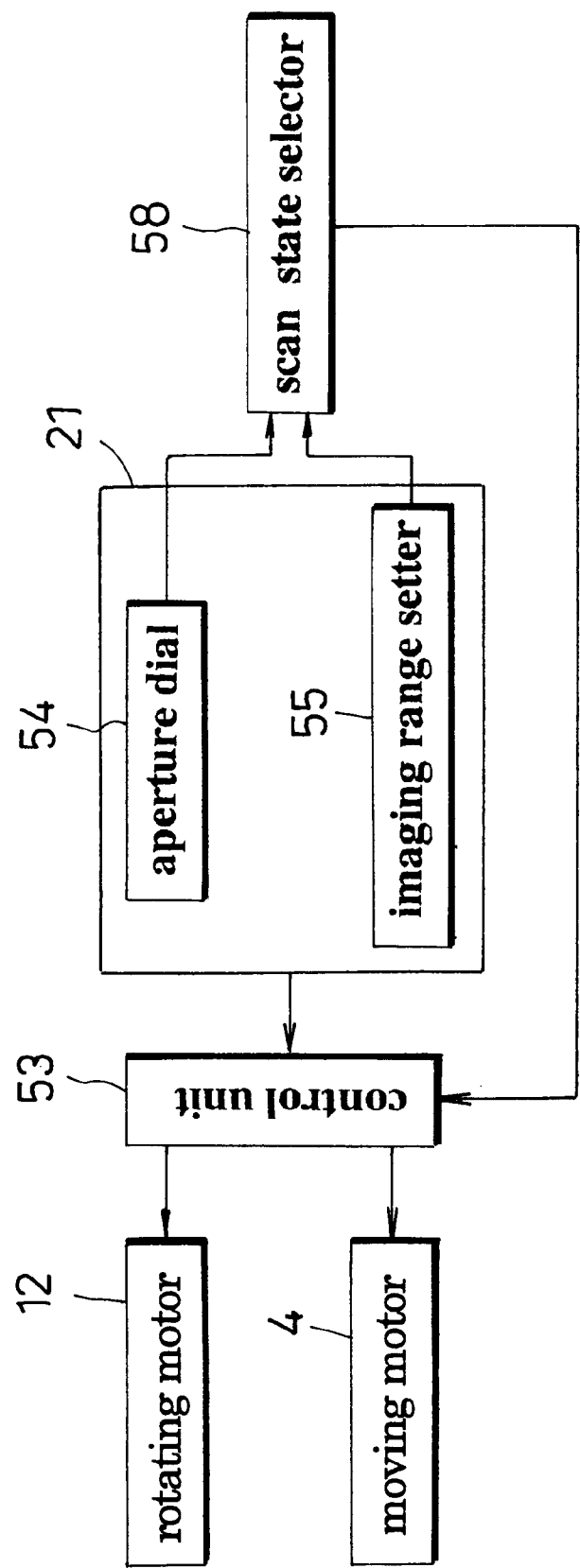
FIG. 18 is a block diagram showing an outline of an X-ray CT apparatus in a third embodiment.

This embodiment differs from the above second embodiment in the following respect. FIG. 18 is a schematic block diagram of this embodiment, in which the size of reconstruct area Pa set by the aperture dial 54 and the imaging range set by the imaging range setter 55 are inputted to a scan mode selector 58.

From the relationship between the size of reconstruct area Pa along the axis of revolution P of X-ray tube 14, i.e. along the body axis Z of patient M, and the imaging range, and based on whether or not the size of reconstruct area Pa along the body axis Z of patient M covers the entire imaging range, the scan mode selector 58 automatically determines and selects the so-called single scan for driving the X-ray tube 14 to emit X rays with the moving motor 4 stopped and only the rotating motor 12 driven, or the so-called spiral scan for driving the X-ray tube 14 to emit X rays while driving the moving motor 4 and rotating motor 12. The scan mode selector 58 inputs a command signal based on the selection made to the control unit 53 which controls the moving motor and rotating motor 12.

As the imaging range is set, the imaging range and the size of reconstruct area Pa set beforehand through the aperture dial 54 are inputted to the scan mode selector 58 for selecting a scan mode.

That is, as shown FIG. 18 illustrating the scan mode selection, the single scan is automatically selected when the size of reconstruct area Pa along the body axis Z of patient M is larger than the imaging range R, and the size of patient M along the body axis Z of patient M covers the entire imaging range R. This includes the case of the imaging range R being wide and the reconstruct area Pa being large along the body axis Z of patient M [see FIG. 19A], and the case of the imaging range R being narrow and the reconstruct area Pa being small along the body axis Z of patient M [see FIG. 19B].

Figure 19A:
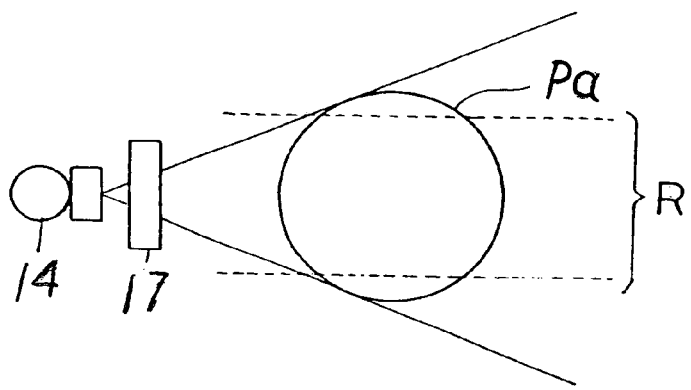
FIG. 19A is an explanatory view showing a case of selecting a single scan when a site of interest fits in a maximum width of a reconstruct area.
Figure 19B:
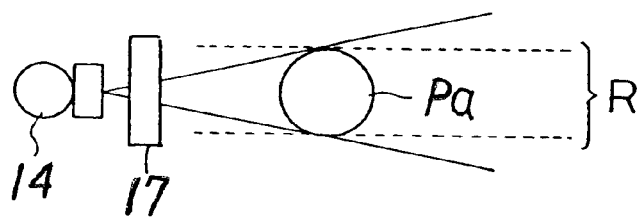
FIG. 19B is an explanatory view showing a case of selecting the single scan when a site of interest has a size fitting in a reconstruct area.
Figure 19C:
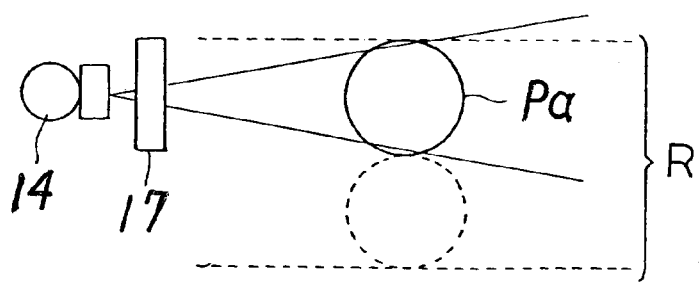
FIG. 19C is an explanatory view showing a case of selecting a spiral scan when a site of interest is larger than a reconstruct area.

The spiral scan is automatically selected when, as shown in FIG. 19C, the reconstruct area Pa is small compared with the imaging range R, the reconstruct area Pa along the body axis Z of patient M is smaller than the imaging range R, and the reconstruct area Pa along the body axis Z of patient M cannot cover the entire imaging range R.

A selection between the single scan and spiral scan may be made automatically based on the relationship in size between the imaging range R and reconstruct area Pa. Thus, images may be picked up of the entire imaging range properly while dispensing with unnecessary X-ray irradiation to reduce the burden of exposure for the patient M.

In the above embodiment, the selection between the single scan and spiral scan is based on a determination whether or not the reconstruct area Pa along the body axis Z of patient M, i.e. along the axis of revolution P of X-ray tube 14, is larger than the imaging range R. This determination is made with reference to whether the reconstruct area Pa along the body axis Z of patient M can cover the entire imaging range R when the X-ray tube 14 is revolved. This invention includes a case, for example, of selecting the single scan when the reconstruct area Pa along the body axis Z of patient M, i.e. along the axis of revolution P of X-ray tube 14, is 1.1 times the imaging range R, and selecting the spiral scan in other times, in order to ensure that the imaging range R is included in the reconstruct area Pa. Thus, even when the reconstruct area Pa is larger than the imaging range R, the spiral scan may be selected for a predetermined range (where the reconstruct area Pa is less than 1.1 times and at lease equal to the imaging range R).

The other aspects of this embodiment are the same as in the second embodiment, and will not be described or shown in the drawings.

In the above embodiment, the reconstruct area Pa is displayed as superimposed on the fluoroscopic image HZ to allow the size of reconstruct area Pa and the imaging range R to be set with ease. This invention is applicable to the following settings and constructions as well:

(1) Neither the aperture motor 52 nor the aperture dial 54 is provided, and the size of reconstruct area Pa is fixed and cannot be changed. In this case, a construction for inputting the fixed size of reconstruct area Pa along the axis of revolution P of X-ray tube 14 to the scan mode selector 58 corresponds to the irradiating field setting device.

(2) Where the reconstruct area Pa is not displayed as superimposed on the fluoroscopic image HZ, for example, the aperture dial 54 is set to a predetermined size in accordance with a site of interest such as the gullet, stomach or abdomen, before an image pickup operation, and only an imaging range is inputted and set as a moving length according to the physique of patient M in time of image pickup. In this case, a scan mode is selected by comparing the size of reconstruct area Pa determined beforehand and the moving length of the imaging range inputted and set.

The present invention may be embodied in other specific forms without departing from the spirit or essential attributes thereof and, accordingly, reference should be made to the appended claims, rather than to the foregoing specification, as indicating the scope of the invention.

What is claimed is:

1. An X-ray CT apparatus for picking up sectional images of an object by irradiating the object with a conical X-ray beam from around a body axis of the object and detecting X rays transmitted through the object, said apparatus comprising:

X-ray image pickup means including an X-ray tube for emitting the conical X-ray beam to said object placed on a top board, and a flat panel X-ray sensor with X-ray detecting elements arranged in a matrix form for detecting transmitted X rays;

drive means for driving the X-ray image pickup means about the body axis of said object;

image reconstruct means for reconstructing a sectional images of a designated section based on transmitted X-ray detection data outputted from said flat panel X-ray sensor of the X-ray image pickup means driven in a fluoroscopic imaging mode;

image display means for displaying X-ray images;

fluoroscopic imaging means for acquiring a fluoroscopic image based on the transmitted X-ray detection data outputted from said flat panel X-ray sensor of the X-ray image pickup means driven in the fluoroscopic imaging mode, and displaying said fluoroscopic image on said image display means; and reconstruct area superimposing means for displaying a reconstruct area for CT imaging as superimposed on said fluoroscopic image acquired by said fluoroscopic imaging means.

2. An apparatus as defined in claim 1, further comprising slice designating means for designating positions of sections for CT imaging on said fluoroscopic image with said reconstruct area superimposed thereon.

3. An apparatus as defined in claim 1, further comprising irradiating area superimposing means for displaying an area irradiated by said conical X-ray beam, as superimposed on said fluoroscopic image.

4. An apparatus as defined in claim 1, further comprising moving means for moving said object along the body axis of said object relative to said X-ray image pickup means.

5. An apparatus as defined in claim 4, further comprising fluoroscopic image composing means for composing and outputting one fluoroscopic image based on transmitted X-ray data corresponding to a plurality of images of said object acquired by driving said moving means to move said object.

6. An apparatus as defined in claim 4, further comprising imaging range setting means for setting an imaging range on said fluoroscopic image displayed on said display means, wherein said moving means is operable to move said object over said imaging range set by said imaging range setting means, and said slice designating means is operable to designate positions of sections within said imaging range.

7. An apparatus as defined in claim 6, further comprising irradiating field setting means for setting a field size of X rays to irradiate said object according to said reconstruct area.

8. An apparatus as defined in claim 7, wherein said irradi-15 ating field setting means includes a collimator and aperture drive means for setting a field size of said conical X-ray beam emitted from said X-ray tube.

9. An apparatus as defined in claim 8, further comprising scan mode selecting means, operable based on the field size of X rays set by said irradiating field setting means and the imaging range set by said imaging range setting means, to select a drive state such that a single scan is carried out by driving said drive means with said moving means stopped when the field size along an axis of revolution of said X-ray image pickup means is larger than the imaging range, and a spiral scan is carried out by simultaneously driving said drive means and said moving means when the field size along the axis of revolution of said X-ray image pickup means is smaller than the imaging range.

* * * * *